United States Patent
Klein (10) Patent No.: US 11,574,711 B1
(45) Date of Patent: Feb. 7, 2023

(54) GRAPHICAL USER INTERFACE METHODOLOGIES FOR PROVIDING SPECIALTY VIEWS OF HEALTHCARE DATA

(71) Applicant: Allscripts Software, LLC, Chicago, IL (US)

(72) Inventor: Mani Klein, Shani Livna (IL)

(73) Assignee: ALTERA DIGITAL HEALTH INC., Chicago, IL (US)

( * ) Notice: Subject to any disclaimer, the term of this patent is extended or adjusted under 35 U.S.C. 154(b) by 1540 days.

(21) Appl. No.: 15/396,641

(22) Filed: Dec. 31, 2016

(51) Int. Cl.
*G16H 10/60* (2018.01)
*G16H 40/63* (2018.01)

(52) U.S. Cl.
CPC ............ *G16H 10/60* (2018.01); *G16H 40/63* (2018.01)

(58) Field of Classification Search
CPC combination set(s) only.
See application file for complete search history.

(56) References Cited

U.S. PATENT DOCUMENTS

| | | | |
|---|---|---|---|
| 2009/0192823 A1* | 7/2009 | Hawkins et al. | |
| 2009/0198514 A1* | 8/2009 | Rhodes | |
| 2012/0215560 A1* | 8/2012 | Ofek et al. | |
| 2013/0166317 A1* | 6/2013 | Beardall | |
| 2013/0191156 A1* | 7/2013 | Upadhyayula et al. | |
| 2014/0330586 A1* | 11/2014 | Riskin et al. | |
| 2015/0278369 A1* | 10/2015 | Wong et al. | |
| 2016/0110505 A1* | 4/2016 | Symanski et al. | |
| 2017/0116373 A1* | 4/2017 | Ginsburg et al. | |
| 2017/0116385 A1* | 4/2017 | Lauderdale et al. | |
| 2017/0300634 A1* | 10/2017 | Chiang et al. | |
| 2018/0018428 A1* | 1/2018 | Coifman | |
| 2018/0107794 A1* | 4/2018 | Fierer et al. | |
| 2018/0150599 A1* | 5/2018 | Valdes et al. | |
| 2018/0181712 A1* | 6/2018 | Ensey et al. | |
| 2018/0181716 A1* | 6/2018 | Mander et al. | |
| 2018/0182475 A1* | 6/2018 | Cossler et al. | |

* cited by examiner

*Primary Examiner* — Michael Tomaszewski
*Assistant Examiner* — William T. Monticello
(74) *Attorney, Agent, or Firm* — Calfee, Halter & Griswold LLP (57) ABSTRACT

A medical software application is configurable to allow different specialty views to be specified for healthcare practitioners having different characteristics (e.g. specialists in different fields), based on, for example, role or specialty information for a logged in user. A specialty view is further be configured to affect the display of data within a domain. A specialty view can specify that a certain vocabulary takes priority for display purposes (e.g. display ordering).

20 Claims, 12 Drawing Sheets

| | Logged in as: Joe White (Cardiothoracic Surgeon) |
|---|---|
| Smith, Sam P. | |
| Age: 73 | Sex M | MRN 933145526 | |

Search

| Active Problems ▽ | Type ▽ | | | |
|---|---|---|---|---|
| Name | | ICD-10 | Managed By | Last Assessed |
| Problems | | | | |
| | Asthma | J45.909 | Dr. Leonard Spock | 09 Oct 2016 |
| | Migraine Headache | G43.909 | Dr. William Kirk | 13 Sep 2016 |

Medications
Problems
Immunizations
Allergies
Orders
»

DUR Alerts:    Drug-Drug (0)    PAR (0)    Disease (0)    Dup Therapy (0)    Dose (0)

*FIG. 1*

Logged in as: Joe White (Cardiothoracic Surgeon)

Smith, Sam P.
Age: 73 | Sex M | MRN 933145526

Search

Active Problems | Type

| Name | ICD-10 | Managed By | Last Assessed |
|---|---|---|---|
| Problems | | | |
| Asthma | J45.909 | Dr. Leonard Spock | 09 Oct 2016 |
| Migraine Headache | G43.909 | Dr. William Kirk | 13 Sep 2016 |

Problems
Immunizations
Allergies
Orders
Procedures

DUR Alerts: Drug-Drug (0)  PAR (0)  Disease (0)  Dup Therapy (0)  Dose (0)

FIG. 2

```
<SpecialtyViews>
  <SpecialtyView name="Cardiothoracic Specialty View" roles="surgeon, headneck, cardiothoracic" IsDefault="false">
    <ClinicalDomains>
      <ClinicalDomain id="procedures"/>
      <ClinicalDomain id="imaging"/>
      <ClinicalDomain id="medications"/>
      <ClinicalDomain id="measurements"/>
      <ClinicalDomain id="orders"/>
    </ClinicalDomains>
  </SpecialtyView>
  ⋮
</SpecialtyViews>
```

*FIG. 3*

| | Logged in as: Joe White (Cardiothoracic Surgeon) |
|---|---|

Smith, Sam P.
Age: 73 | Sex M | MRN 933145526

| Procedures | All Procedures ▽ | Type ▽ | | |
|---|---|---|---|---|
| Imaging | Name | | Code | Managed By | Performed |
| Medications | Procedures | | | | |
| Measurements | Wisdom Teeth Removal | | D7210 | Frank Bones, DMD | 04 Feb 1985 |
| Orders | Thorax Procedure | | T1546 | Joe White, MD | 04 Feb 1985 |
| ≫ | | | | | |

DUR Alerts: Drug-Drug (0)　PAR (0)　Disease (0)　Dup Therapy (0)　Dose (0)

*FIG. 4*

```
<SpecialtyViews>

<SpecialtyView name="Cardiothoracic Specialty View" roles="surgeon, headneck, cardiothoracic" IsDefault="false">
    <ClinicalDomains>
        <ClinicalDomain id="procedures"/>
        <ClinicalDomain id="imaging"/>
        <ClinicalDomain id="medications"/>
        <ClinicalDomain id="measurements"/>
        <ClinicalDomain id="orders"/>
    </ClinicalDomains>
</SpecialtyView>

<SpecialtyView name="Internist Specialty View" roles="internist" IsDefault="true">
    <ClinicalDomains>
        <ClinicalDomain id="problems"/>
        <ClinicalDomain id="immunizations"/>
        <ClinicalDomain id="allergies"/>
        <ClinicalDomain id="orders"/>
        <ClinicalDomain id="procedures"/>
    </ClinicalDomains>
</SpecialtyView>

⋮

</SpecialtyViews>
```

FIG. 5

| Smith, Sam P. | | | Logged in as: Jeff Green (Internist) |
|---|---|---|---|
| Age: 73 \| Sex M \| MRN 933145526 | | Search | |

| | Active Problems ▽ | Type ▽ | | |
|---|---|---|---|---|
| Problems | Name | ICD-10 | Managed By | Last Assessed |
| | Problems | | | |
| Immunizations | Asthma | J45.909 | Dr. Leonard Spock | 09 Oct 2016 |
| | Migraine Headache | G43.909 | Dr. William Kirk | 13 Sep 2016 |
| Allergies | | | | |
| Orders | | | | |
| Procedures | | | | |

DUR Alerts:  Drug-Drug (0)  PAR (0)  Disease (0)  Dup Therapy (0)  Dose (0)

*FIG. 6*

```
<SpecialtyViews>
<SpecialtyView name="Cardiothoracic Specialty View" roles="surgeon, headneck, cardiothoracic" IsDefault="false">
    <ClinicalDomains>
        <ClinicalDomain id="procedures" vocabulary_priorities="ThoraxProcedure,SurgicalProcedure"/>
        <ClinicalDomain id="imaging" vocabulary_priorities="ThoraxProcedure,SurgicalProcedure"/>
        <ClinicalDomain id="medications" vocabulary_priorities=""/>
        <ClinicalDomain id="measurements" vocabulary_priorities=""/>
        <ClinicalDomain id="orders" vocabulary_priorities=""/>
    </ClinicalDomains>
</SpecialtyView>
    ...
</SpecialtyViews>
```

FIG. 7

| | Logged in as: Joe White (Cardiothoracic Surgeon) |
|---|---|

Smith, Sam P.
Age: 73 | Sex M | MRN 933145526

[Search]

| | | | ⊕ |

| Procedures | All Procedures ▽ | Type ▽ | | |
|---|---|---|---|---|
| Imaging | Name | Code | Managed By | Performed |
| Medications | Procedures | | | |
| Measurements | ▦ Thorax Procedure | T1546 | Joe White, MD | 04 Feb 1985 |
| Orders | ▦ Wisdom Teeth Removal | D7210 | Frank Bones, DMD | 04 Feb 1985 |
| ≫ | | | | |

| DUR Alerts: | Drug-Drug (0) | PAR (0) | Disease (0) | Dup Therapy (0) | Dose (0) |

| Smith, Sam P. | | | | Logged in as: Joe White (Cardiothoracic Surgeon) |
|---|---|---|---|---|
| Age: 73 \| Sex M \| MRN 9331145526 | | | Search | |

| Procedures | Imaging | Meds | Measurements | Orders | Allergies |
|---|---|---|---|---|---|

| All Procedures ▽ | Type ▽ | | |
|---|---|---|---|
| Name | Code | Managed By | Performed |
| Procedures | | | |
| Wisdom Teeth Removal | D7210 | Frank Bones, DMD | 04 Feb 1985 |
| Thorax Procedure | T1546 | Joe White, MD | 04 Feb 1985 |

DUR Alerts:    Drug-Drug (0)    PAR (0)    Disease (0)    Dup Therapy (0)    Dose (0)

*FIG. 10*

Smith, Sally A.
Age: 31 | Sex F | MRN 933145526

Medical History

Active Problems
Type II Diabetes Mellitus (250.00) – w/o mention of complication or manifestation; type II, controlled
Managed by – SMITH, John MD | Onset Date – 16-May-2008
Hypertension (401.0) – Essential hypertension; malignant
Seasonal Allergic Reaction (477.0) – Allergic rhinitis, due to pollen, Pollinosis

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

---

Smith, Sally A.
31y | Female | 933145526

▽ Clinical Information
△ Procedures
△ Imaging
△ Medications
△ Measurements
△ Labs
△ Allergies
△ Encounters
△ Problems
△ Diagnoses
△ Pathology
△ Immunizations
△ Documents
△ External Documents Joe White (Cardiothoracic Surgeon)    EHR Agent

GRAPHICAL USER INTERFACE METHODOLOGIES FOR PROVIDING SPECIALTY VIEWS OF HEALTHCARE DATA

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to graphical user interface methodologies for displaying clinical data to a healthcare practitioner.

Figure 1:
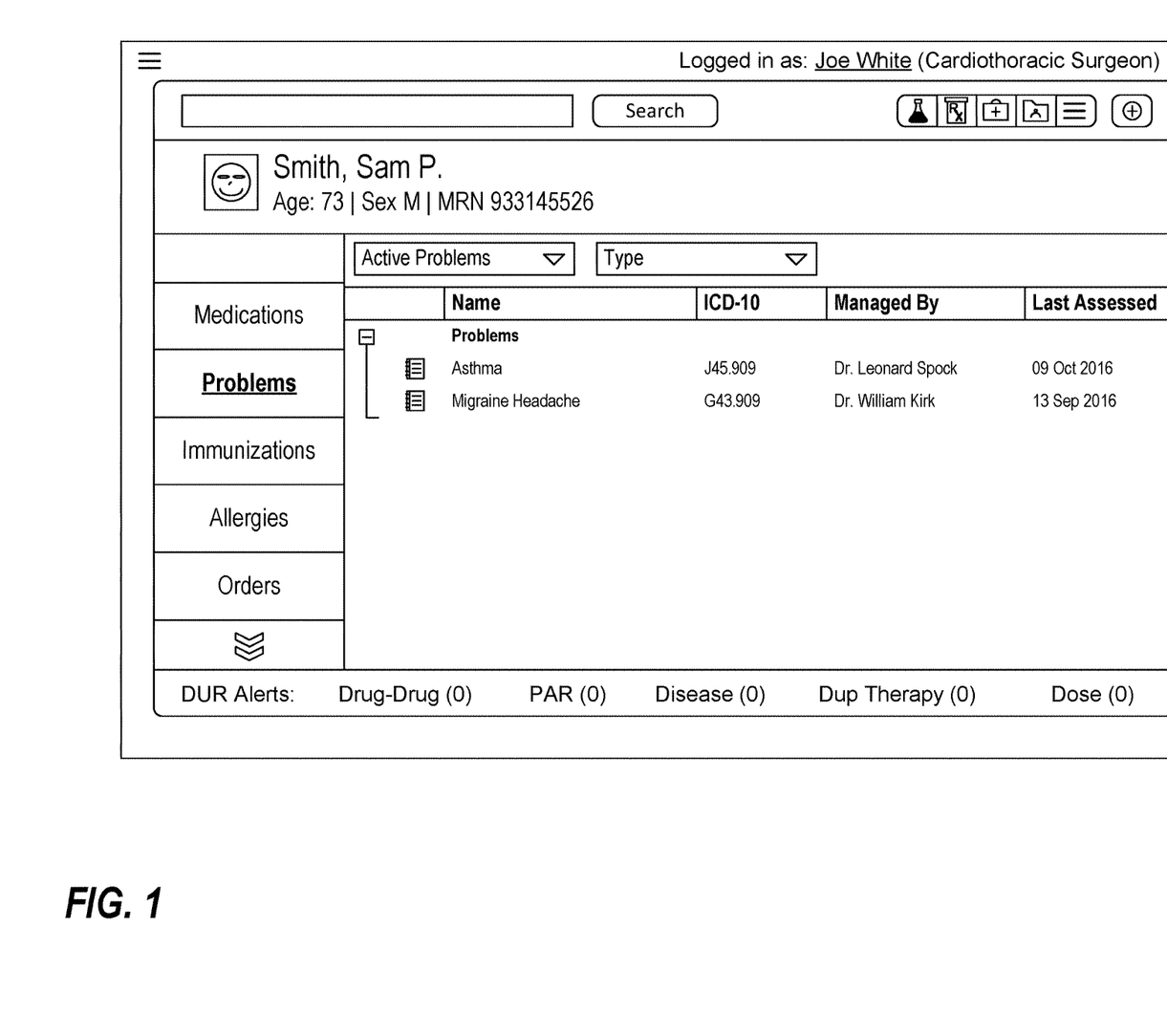
FIGS. 1-2 illustrates an interface of an exemplary EHR application which is displaying healthcare information for a patient in a problems domain.

Electronic healthcare record (EHR) applications are ubiquitous in the healthcare industry. Typically, EHR applications display healthcare information for a patient organized into a plurality of domains, such as problems, medications, encounters, procedures, etc. For example, FIG. 1 illustrates an interface of an exemplary EHR application which is displaying healthcare information for a patient in a problems domain.

An interface of an EHR application typically provides a way for a user to review information from these different domains, e.g. by browsing between different domains. For example, the interface of FIG. 1 includes a scrollable menu on the left side of the screen which allows a user to select different domains to view information for.

Figure 2:
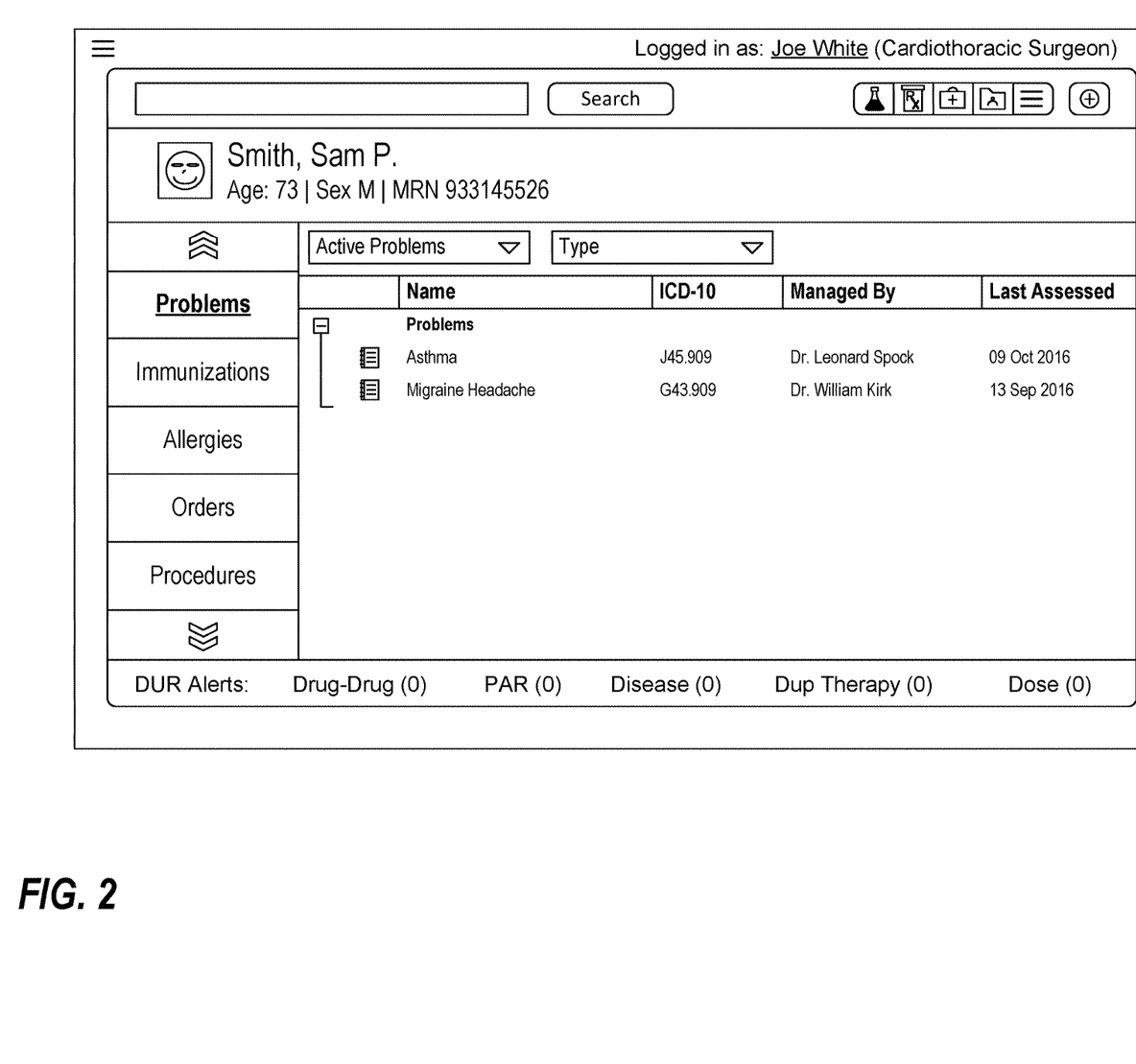

Notably, however, not all healthcare practitioners have the same clinical interests. For example, the logged-in, a cardiothoracic surgeon, may have much more interest in a procedures domain than another practitioner, who might have more interest in the problems domain. With reference to the interface of FIG. 1, however, a logged-in cardiothoracic surgeon cannot even access the procedures domain without first scrolling through the menu, as illustrated in FIG. 2.

A need exists for improvement in graphical user interface methodologies for displaying clinical data to a healthcare practitioner. This, and other needs, are addressed by one or more aspects of the present invention.

SUMMARY OF THE INVENTION

The present invention includes many aspects and features. Moreover, while many aspects and features relate to, and are described in, the context of apparatus, systems, and methods pertaining to electronic healthcare records, the present invention and advantages thereof are not limited to use only in such context, as will become apparent from the following summaries and detailed descriptions of aspects, features, and one or more embodiments of the present invention.

Accordingly, in an aspect of the invention, a method for providing, in a graphical user interface (GUI) of an electronic healthcare records (EHR) application running at an electronic device, specialty views of healthcare data comprises: (a) receiving, at the EHR application from the user via one or more input devices associated with the electronic device, first user input corresponding to login credentials for a user account of the user; (b) determining, by the EHR application, a first role associated with the user account of the user; (c) accessing, by the EHR application, configuration information for a plurality of specialty views, the configuration information for each respective specialty view including (i) an indication of one or more roles associated with the respective specialty view, and (ii) an indication of the relative priority of each clinical domain in a first set of one more clinical domains specified for that respective specialty view, and (iii) for each respective clinical domain of one or more of the clinical domains of the first set of clinical domains for that respective specialty view, an indication of the relative priority of each vocabulary in a first set of one more vocabularies specified for that respective clinical domain; (d) comparing, by the EHR application, the first role associated with the user account with roles associated with specialty views in the accessed configuration information; (e) determining, by the EHR application based on the comparison of the first role to roles associated with specialty views, that a first specialty view of the plurality of specialty views should be utilized; (f) determining, by the EHR application based on the relative priority of clinical domains defined for the first specialty view in configuration information for the first specialty view, an ordering of clinical domains for display to the user; (g) displaying, to the user via an electronic display associated with the electronic device, a first interface of the EHR application which includes a listing of clinical domains ordered in the determined order; (h) receiving, at the EHR application from the user via one or more input devices associated with the electronic device, second user input corresponding to an indication to access information for a first clinical domain of the displayed clinical domains; (i) determining, by the EHR application based on the relative priority of vocabularies defined with respect to the clinical domain for the first specialty view in configuration information for the first specialty view, an ordering of clinical items for display to the user; and (j) displaying in the first interface, to the user via the electronic display in response to the received first user input corresponding to an indication to access information for the first clinical domain, a listing of clinical items associated with the first clinical domain, the clinical items being ordered in the determined order.

In a feature of this aspect, the electronic device comprises a desktop.

In a feature of this aspect, the electronic device comprises a laptop.

In a feature of this aspect, the electronic device comprises a touchscreen device.

In a feature of this aspect, the electronic device comprises a mobile device.

In a feature of this aspect, the electronic device comprises a tablet.

In a feature of this aspect, the electronic device comprises a phone.

In a feature of this aspect, the displayed listing of clinical domains includes a clinical domain associated with diagnoses.

In a feature of this aspect, the displayed listing of clinical domains includes a clinical domain associated with encounters.

In a feature of this aspect, the displayed listing of clinical domains includes a clinical domain associated with procedures.

In a feature of this aspect, the displayed listing of clinical domains includes a clinical domain associated with problems.

In a feature of this aspect, the displayed listing of clinical domains includes a clinical domain associated with allergies.

In a feature of this aspect, the displayed listing of clinical domains includes a clinical domain associated with immunizations.

In another aspect, one or more computer readable media contains computer executable instructions for performing a method for providing, in a graphical user interface (GUI) of an electronic healthcare records (EHR) application running at an electronic device, specialty views of healthcare data. This method comprises: (a) receiving, at the EHR application from the user via one or more input devices associated with the electronic device, first user input corresponding to login credentials for a user account of the user; (b) determining, by the EHR application, a first role associated with the user account of the user; (c) accessing, by the EHR application, configuration information for a plurality of specialty views, the configuration information for each respective specialty view including (i) an indication of one or more roles associated with the respective specialty view, and (ii) an indication of the relative priority of each clinical domain in a first set of one more clinical domains specified for that respective specialty view, and (iii) for each respective clinical domain of one or more of the clinical domains of the first set of clinical domains for that respective specialty view, an indication of the relative priority of each vocabulary in a first set of one more vocabularies specified for that respective clinical domain; (d) comparing, by the EHR application, the first role associated with the user account with roles associated with specialty views in the accessed configuration information; (e) determining, by the EHR application based on the comparison of the first role to roles associated with specialty views, that a first specialty view of the plurality of specialty views should be utilized; (f) determining, by the EHR application based on the relative priority of clinical domains defined for the first specialty view in configuration information for the first specialty view, an ordering of clinical domains for display to the user; (g) displaying, to the user via an electronic display associated with the electronic device, a first interface of the EHR application which includes a listing of clinical domains ordered in the determined order; (h) receiving, at the EHR application from the user via one or more input devices associated with the electronic device, second user input corresponding to an indication to access information for a first clinical domain of the displayed clinical domains; (i) determining, by the EHR application based on the relative priority of vocabularies defined with respect to the clinical domain for the first specialty view in configuration information for the first specialty view, an ordering of clinical items for display to the user; and (j) displaying in the first interface, to the user via the electronic display in response to the received first user input corresponding to an indication to access information for the first clinical domain, a listing of clinical items associated with the first clinical domain, the clinical items being ordered in the determined order.

In a feature of this aspect, the displayed listing of clinical domains includes a clinical domain associated with diagnoses.

In a feature of this aspect, the displayed listing of clinical domains includes a clinical domain associated with encounters.

In a feature of this aspect, the displayed listing of clinical domains includes a clinical domain associated with procedures.

In a feature of this aspect, the displayed listing of clinical domains includes a clinical domain associated with problems.

In a feature of this aspect, the displayed listing of clinical domains includes a clinical domain associated with allergies.

In a feature of this aspect, the displayed listing of clinical domains includes a clinical domain associated with immunizations.

In addition to the aforementioned aspects and features of the present invention, it should be noted that the present invention further encompasses the various logical combinations and subcombinations of such aspects and features. Thus, for example, claims in this or a divisional or continuing patent application or applications may be separately directed to any aspect, feature, or embodiment disclosed herein, or combination thereof, without requiring any other aspect, feature, or embodiment.

BRIEF DESCRIPTION OF THE DRAWINGS

One or more preferred embodiments of the present invention now will be described in detail with reference to the accompanying drawings, wherein the same elements are referred to with the same reference numerals.

DETAILED DESCRIPTION

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention, and is made merely for the purposes of providing a full and enabling disclosure of the invention.

The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard solely to construction of any claim with respect to the United States, no claim element is to be interpreted under 35 U. S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once during performance of the claimed method.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." When used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the invention are next described. The following description of one or more preferred embodiments is merely exemplary in nature and is in no way intended to limit the invention, its implementations, or uses.

As discussed hereinabove, an interface of an EHR application typically provides a way for a user to review information from different domains, but not all healthcare practitioners have the same clinical interests. A view, or interface configuration, that is ideal for one healthcare practitioner may be less useful for another.

As noted above, the interface of FIG. 1 includes a scrollable menu on the left side of the screen which allows a user to select different domains to view information for, but a logged in cardiothoracic surgeon who has generally has interest in a procedures domain has to scrolling before he can even access the procedures domain, as illustrated in FIG. 2.

In accordance with one or more preferred implementations, a medical software application is configurable to allow different specialty views to be specified for healthcare practitioners having different characteristics (e.g. specialists in different fields), based on, for example, role or specialty information for a logged in user.

Figure 3:
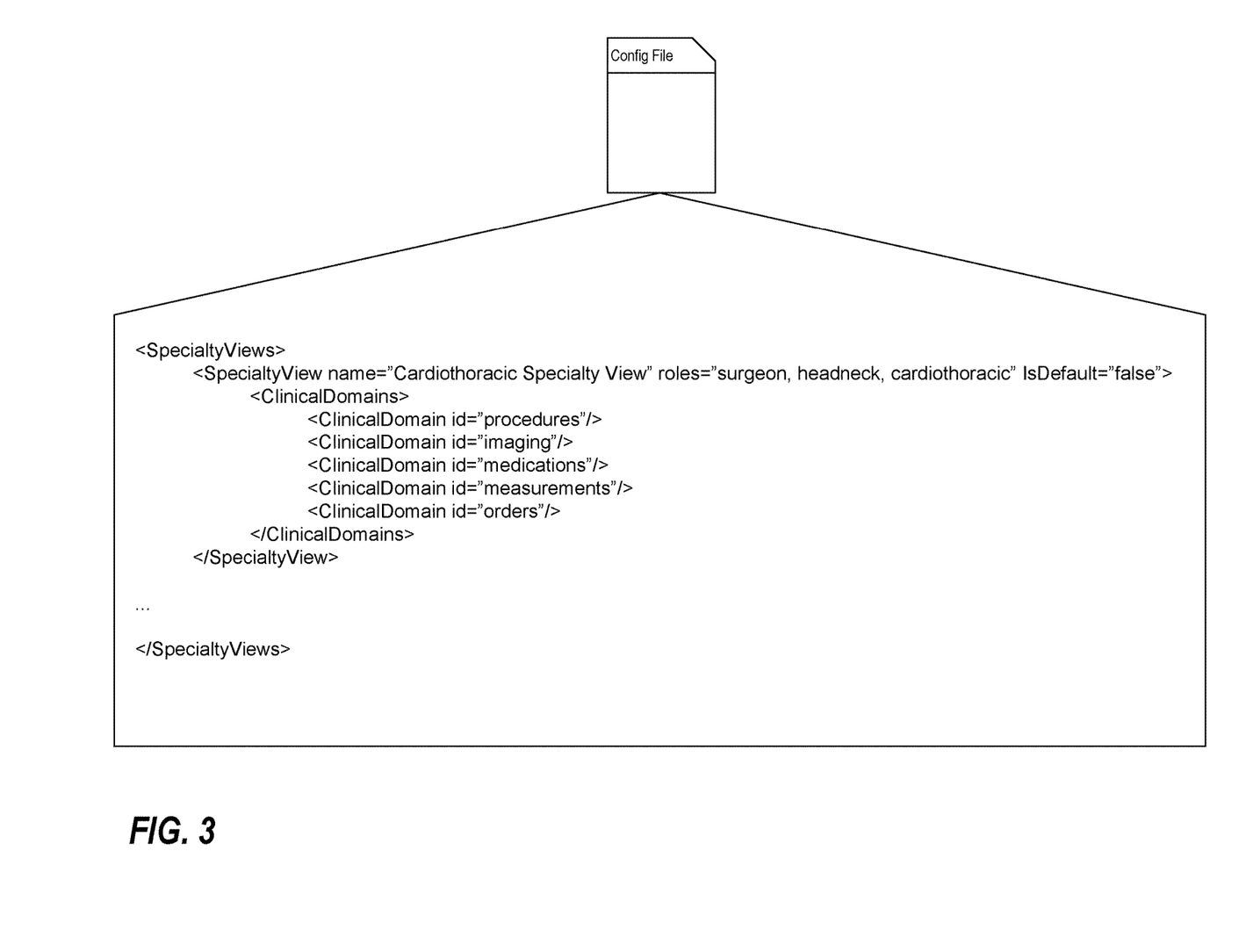
FIG. 3 illustrates an exemplary configuration file which defines a first specialty view for logged in users having a role matching one of the specified roles.

FIG. 3 illustrates an exemplary configuration file for the exemplary EHR application of FIG. 1 which defines a first specialty view for logged in users having a role matching one of the specified roles. The first specialty view is defined as a "Cardiothoracic Specialty View", and is associated with the roles "surgeon", "headneck", and "cardiothoracic". The first specialty view defines an ordering of domains for users having a role matching one of the specified roles.

Figure 4:
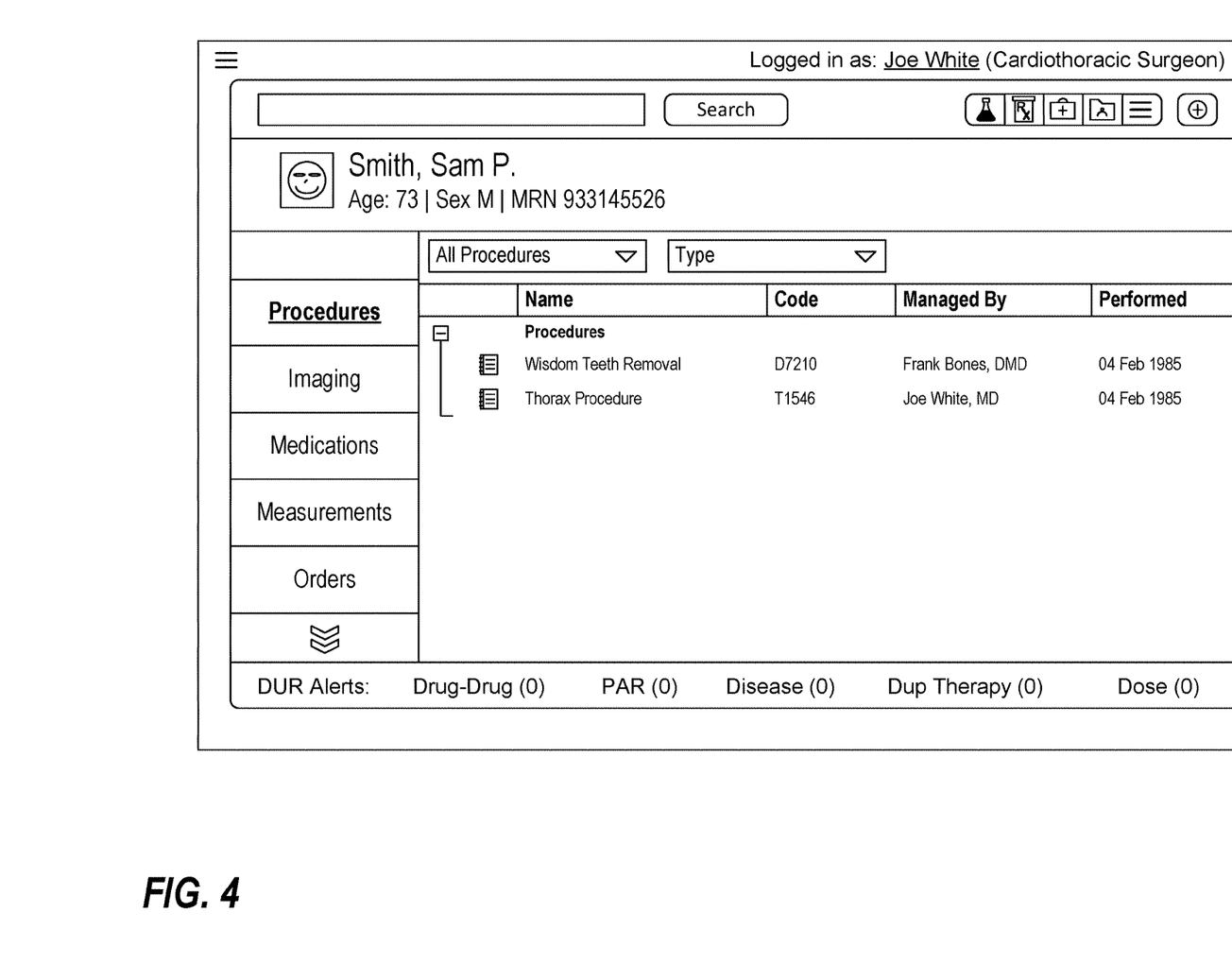
FIG. 4 illustrates ordering of displayed domains based on the configuration file of FIG. 3.

When a user having a role matching one of the specified roles in the first specialty view logs in to the EHR application, the domains are ordered in accordance with the first specialty view, as illustrated in FIG. 4, where the displayed domains have been reordered, e.g. listing a procedures domain first.

Figure 5:
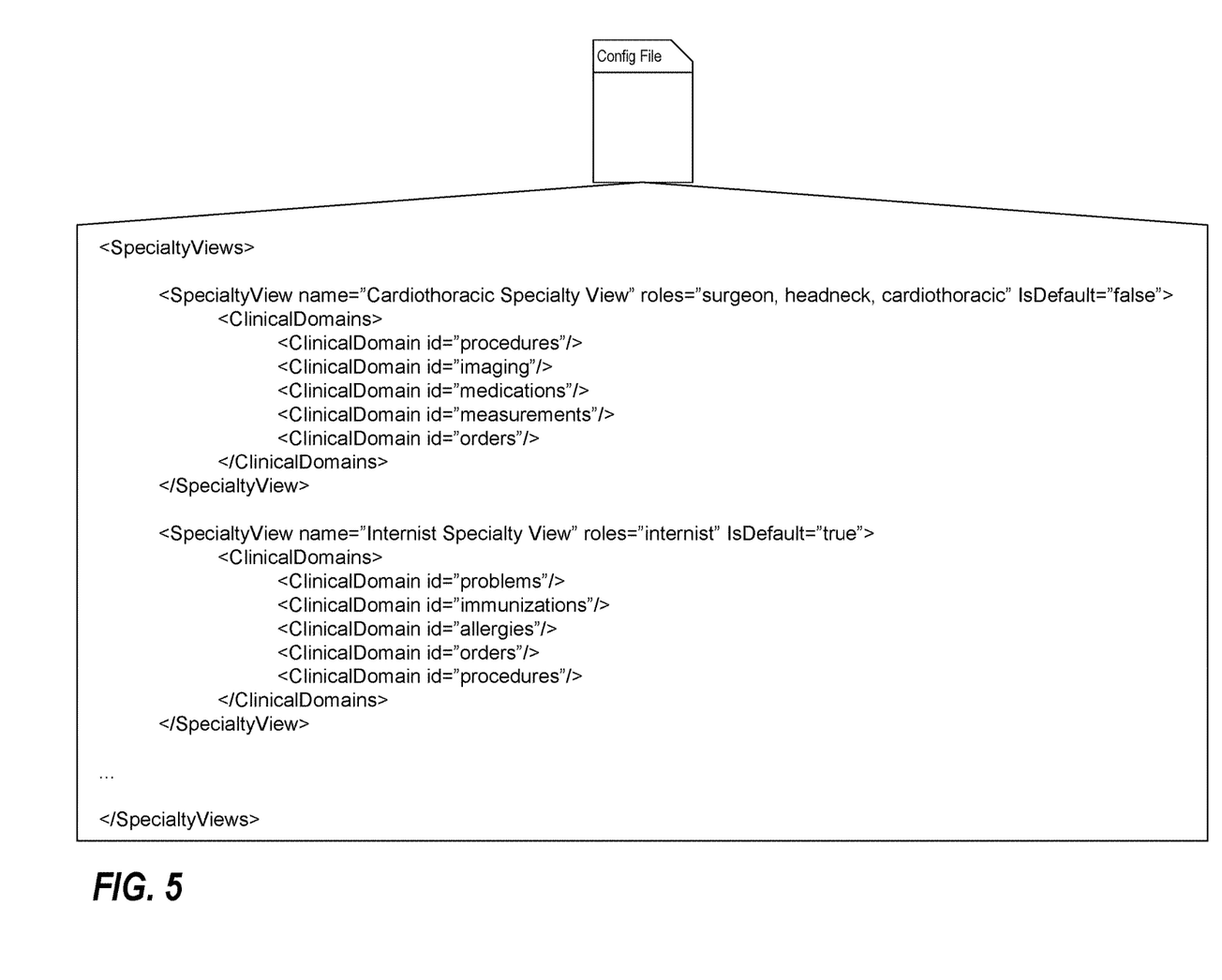
FIG. 5 illustrates an exemplary configuration file which defines a second specialty view for logged in users having a role matching a specified role.

In accordance with one or more preferred implementations, multiple different specialty views may be defined in a configuration file, and a specialty view may even be marked as the default view, as illustrated in FIG. 5. In FIG. 5, a second specialty view is defined as a "Internist Specialty View", and is associated with the role "internist", but is further indicated to be the default view for users whose role does not match a defined specialty view.

Figure 6:
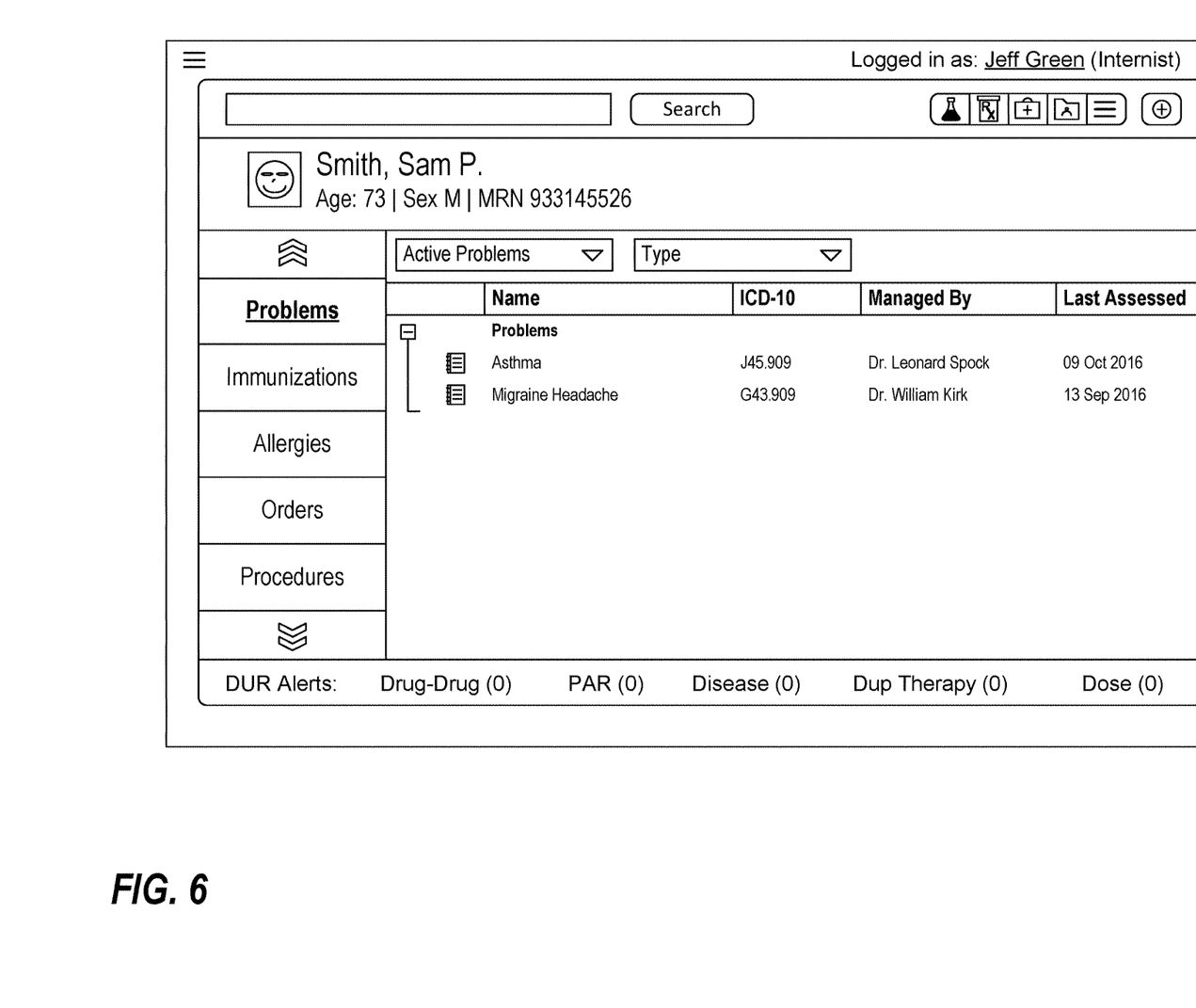
FIG. 6 illustrates ordering of displayed domains based on the configuration file of FIG. 5.

When a user having a role matching one of the specified roles logs in to the EHR application, the domains are ordered in accordance with the second specialty view, as illustrated in FIG. 6.

In accordance with one or more preferred implementations, a specialty view can further be configured to affect the display of data within a domain. In accordance with one or more preferred implementations, a specialty view might specify that a certain vocabulary takes priority for display purposes (e.g. display ordering).

Figure 7:
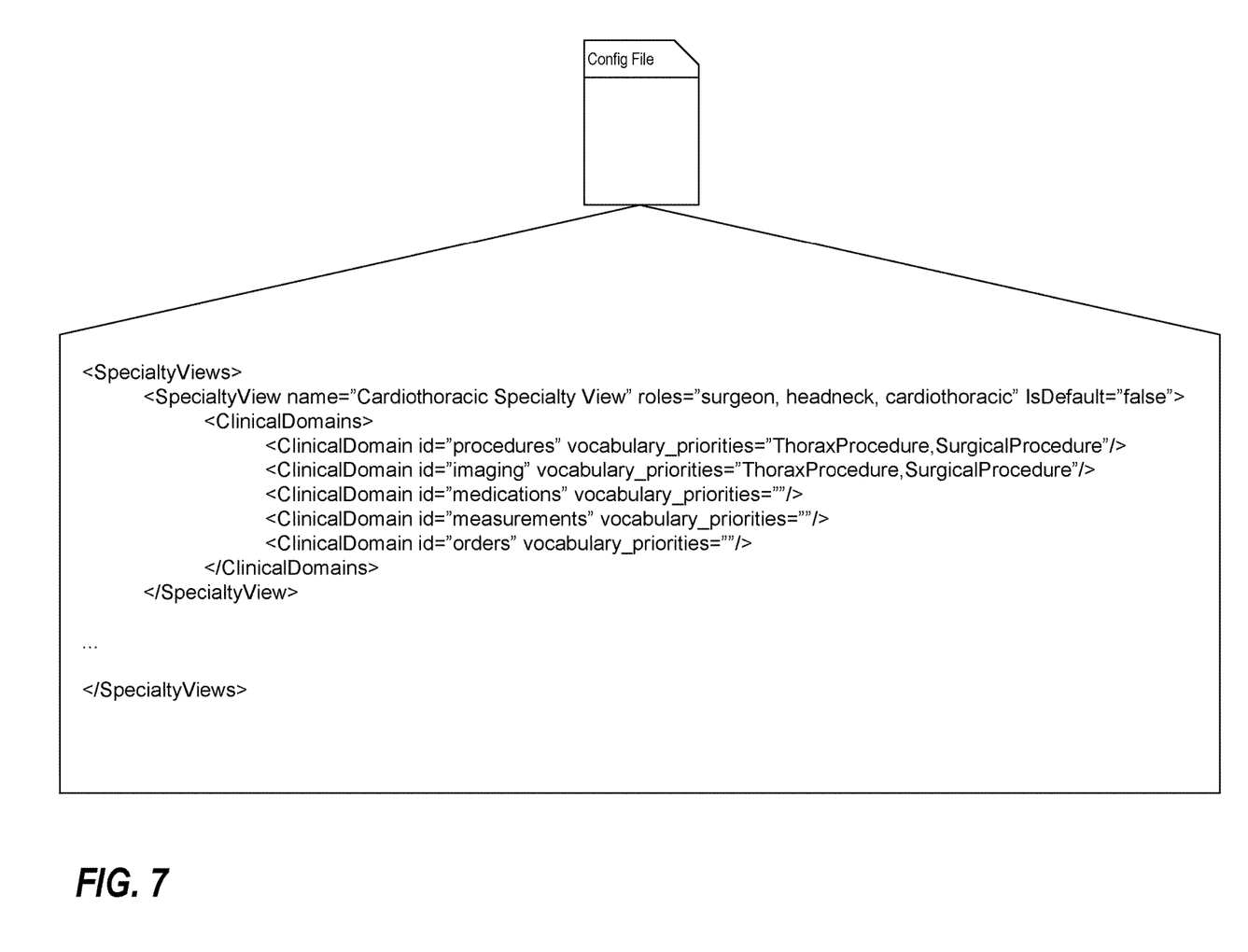
FIG. 7 illustrates an exemplary configuration file which specifies the relative priority of vocabularies within clinical domains.
Figure 8:
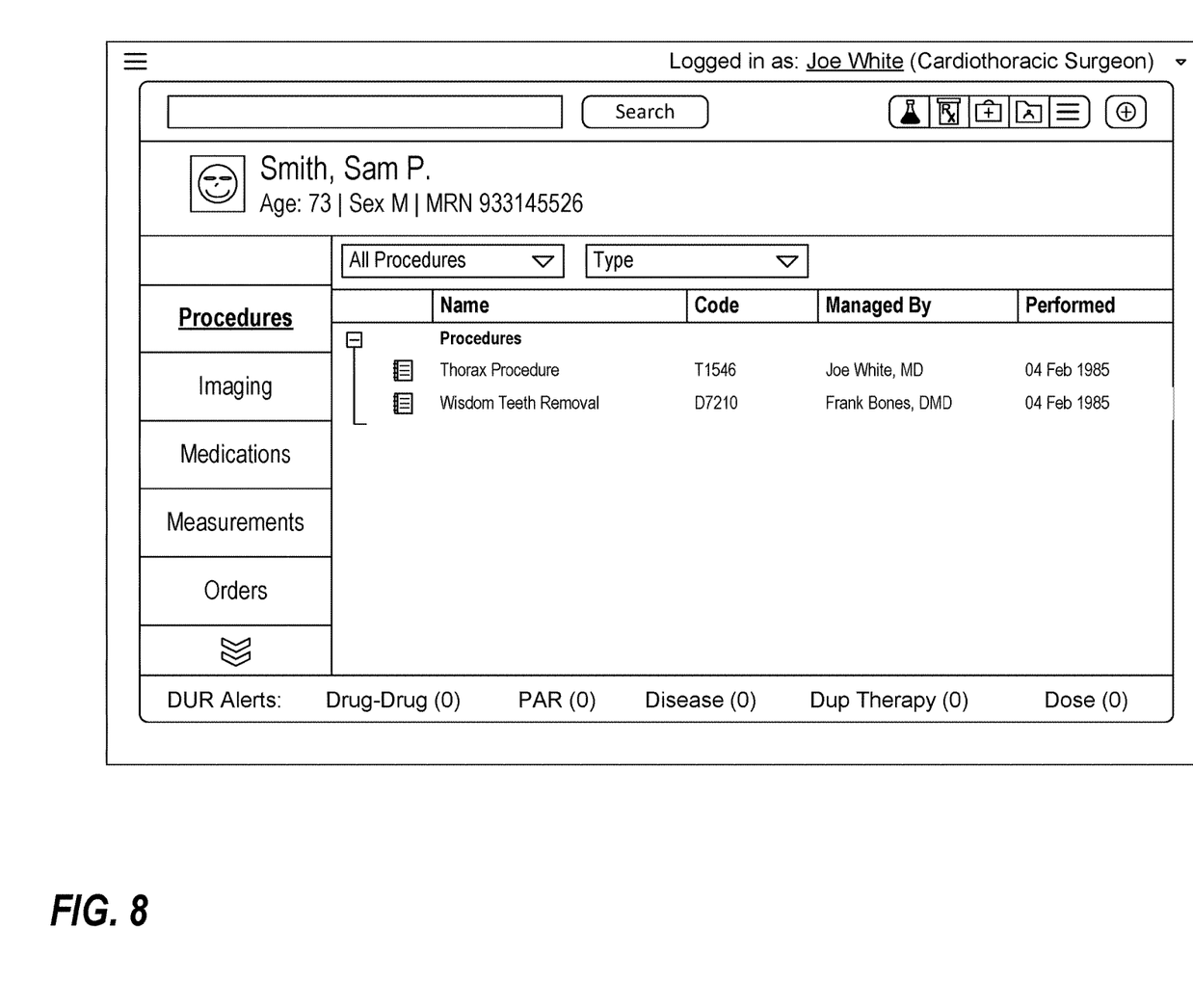
FIG. 8 illustrates ordering of displayed clinical items based on the configuration file of FIG. 5.

In FIG. 7, the first specialty view is further defined to specify that within the procedures domain, the vocabulary "ThoraxProcedure" has first priority, and the vocabulary "SurgicalProcedure" has second priority. In accordance with one or more preferred implementations, this causes displayed procedures to be ordered such that procedures matching these vocabularies are displayed first, in order of priority. For example, FIG. 8 illustrates display of procedures with this updated first specialty view, where the ordering of the displayed procedures has been updated to list the a thorax procedure first based on the thorax procedure matching a vocabulary specified in the vocabulary priority field of the updated first specialty view.

Figure 9:
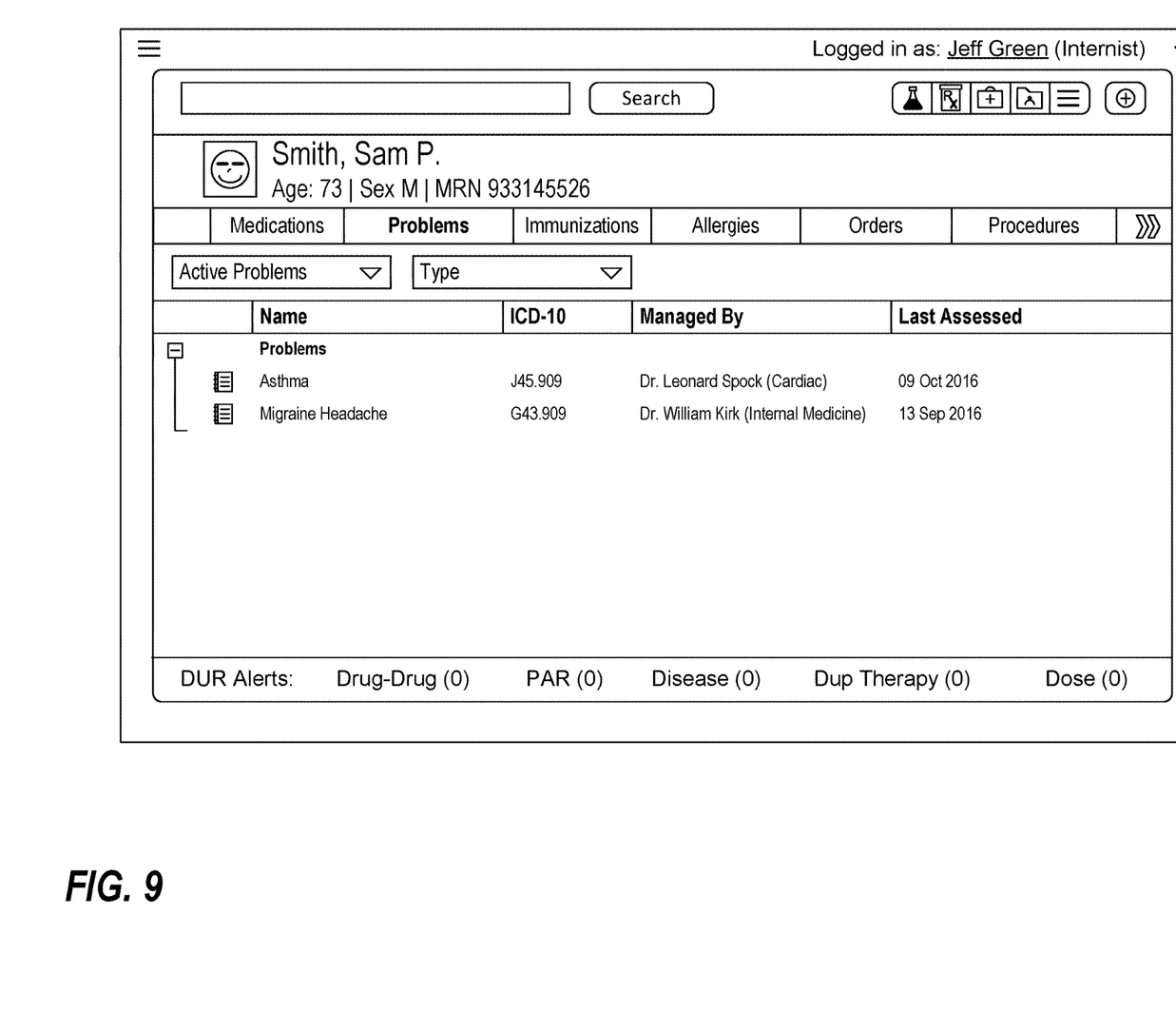
FIGS. 9-10 illustrate use of specialty views for an exemplary EHR application in which domain selection is provided by a horizontal, rather than a vertical, menu.
Figure 10:
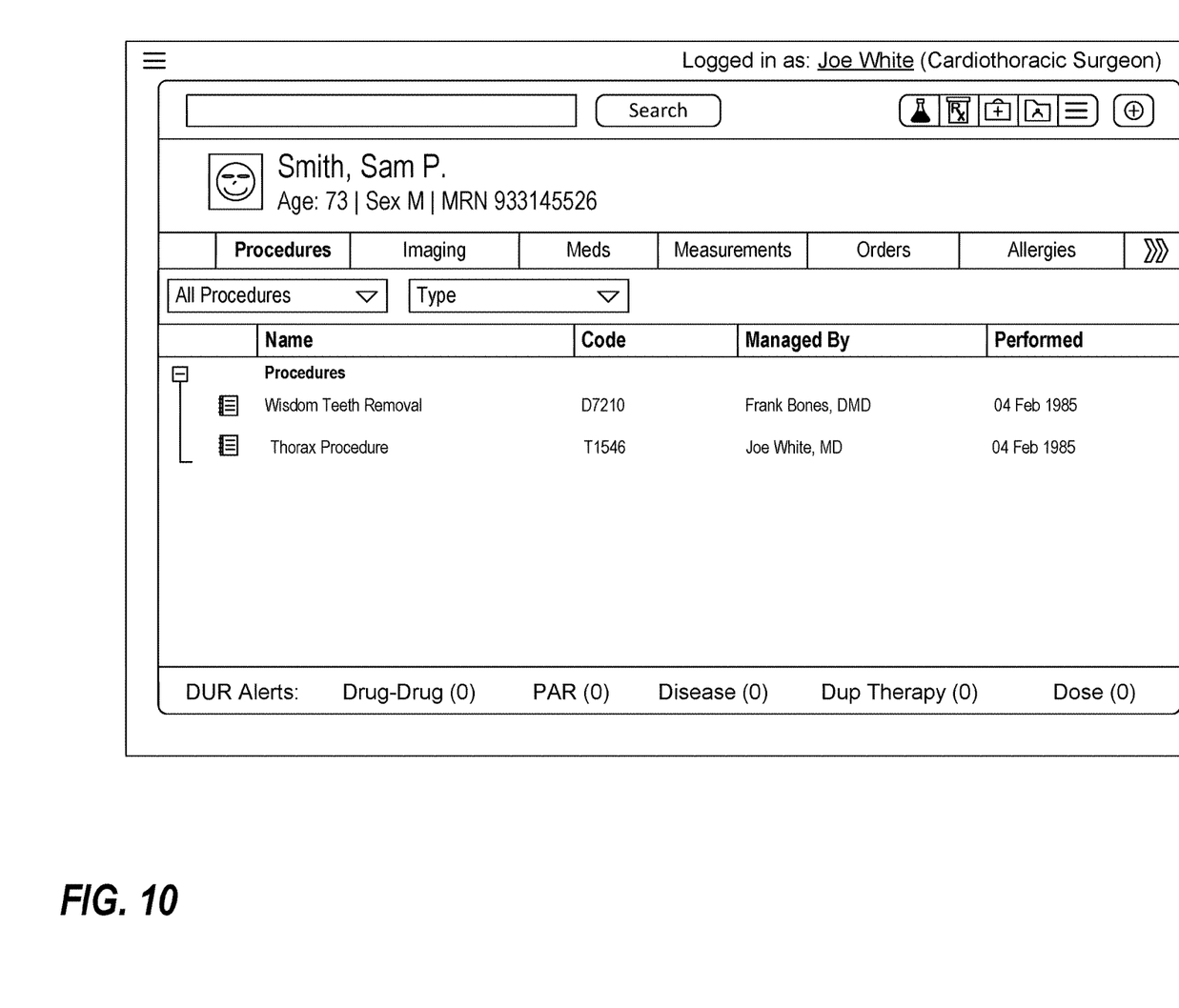

It will be appreciated that although methodologies disclosed herein for providing specialty views based on one or more characteristics (e.g. a role) of a logged in user are described in the context of an exemplary EHR application, such methodologies could equally be utilized with other healthcare software. For example, FIGS. 9-10 illustrate use of specialty views for another exemplary EHR application in which domain selection is provided by a horizontal, rather than a vertical, menu.

Figure 11:
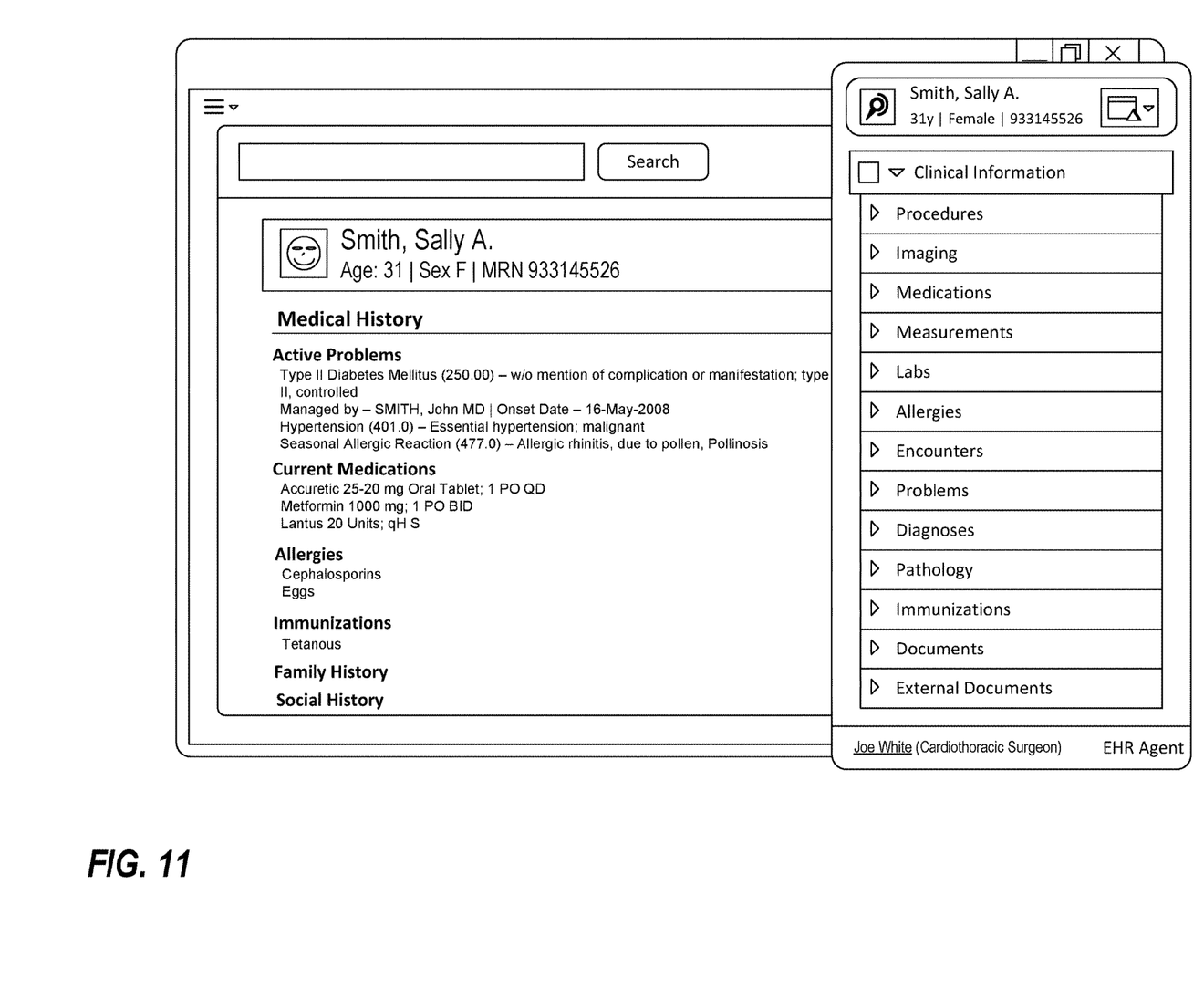
FIGS. 11-12 illustrate use of specialty views for an EHR agent, or Health Information Exchange (HIE) agent.
Figure 12:
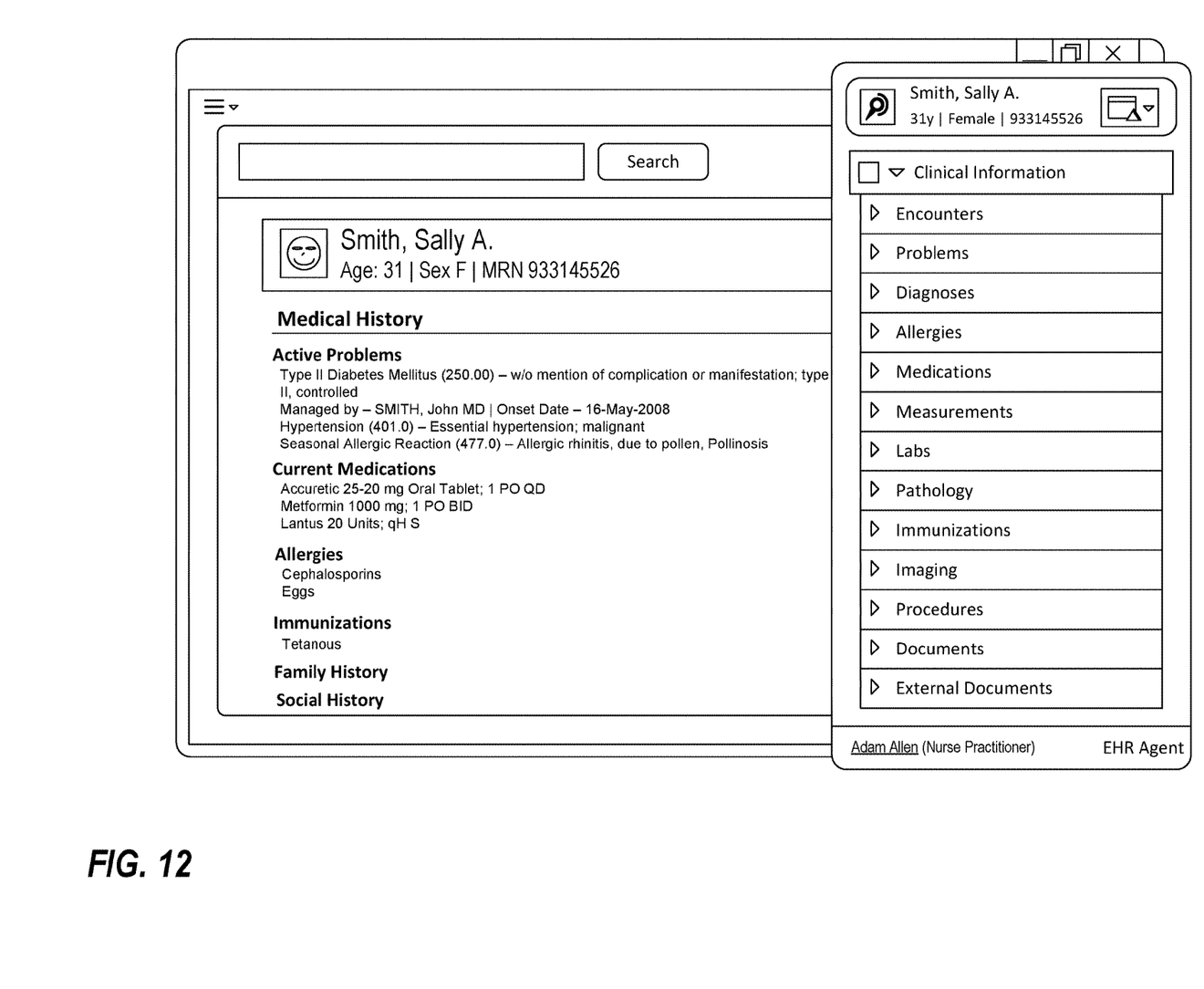

As another example, FIGS. 11-12 illustrate use of specialty views for an EHR agent, or Health Information Exchange (HIE) agent, which is designed to sit on top of existing EHR software in an EHR agnostic manner A system including such an agent is disclosed, for example, in U.S. Patent Application Pub. No. 2012/0215560, which patent application publication is hereby incorporated herein by reference. In accordance with one or more preferred implementations, a system aggregates data from a plurality of sources, including a plurality of EHR systems, and includes an EHR agent which comprises a graphical interface designed to overlay an EHR interface and provide information that may not be present in the EHR. The system preferably intercepts context from an EHR application (such as a current patient for which data is being displayed), and uses such intercepted context to select data for display in an agent interface.

In accordance with one or more preferred implementations, a system aggregates data from one or more sources, such as EHR systems or databases, patient portals, third party applications, payer systems and databases, and payer transaction processor systems. In accordance with one or more preferred implementations, a system stores aggregated information as community information, and aggregated community information is accessed by an EHR agent. Additionally or alternatively, in accordance with one or more preferred implementations, an EHR agent is configured to access information from multiple sources and aggregate information in real time at time of access.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for providing, in a graphical user interface of an electronic healthcare records (EHR) application executed by a processor of an electronic device, specialty views of healthcare data, the method comprising:

receiving, at the EHR application, first input from a user, the first input corresponding to login credentials for a user account of the user;

determining, by the EHR application and based upon the first input, a role associated with the user account of the user;

accessing, by the EHR application, configuration information for a specialty view in a plurality of specialty views, the configuration information for the specialty view including:

an indication that the specialty view is associated with the role, wherein the specialty view has a first clinical domain and a second clinical domain assigned thereto;

an indication that the first clinical domain has a first priority and the second clinical domain has a second priority for the specialty view, wherein the first priority is higher than the second priority, and further wherein the first clinical domain has a first vocabulary and a second vocabulary assigned thereto; and an indication that the first vocabulary has a third priority and the second vocabulary has a fourth priority for the clinical domain, wherein the third priority is higher than the fourth priority;

comparing, by the EHR application, the role associated with the user account with the role associated with the specialty view in the configuration information;

determining, by the EHR application and based on the comparing, that the specialty view in the plurality of specialty views is to be utilized;

determining, by the EHR application and based on the first clinical domain having the first priority for the specialty view and the second clinical domain having the second priority for the specialty view, an ordering of the first clinical domain and the second clinical domain for display;

displaying, in an interface of the EHR application presented on an electronic display associated with the electronic device and according to the ordering of the clinical domains, a first identifier for the first clinical domain and a second identifier for the second clinical domain;

receiving, at the EHR application, second input from the user, the second input corresponding to an indication to access information for the first clinical domain;

determining, by the EHR application and based on the first vocabulary having the first priority for the clinical domain and the second vocabulary having the second priority for the clinical domain, an ordering of clinical items for display; and displaying, in the interface of the EHR application and based upon the ordering of the clinical items, an identifier for the each of the clinical items.

2. The method of claim 1, wherein the electronic device comprises a desktop.

3. The method of claim 1, wherein the electronic device comprises a laptop.

4. The method of claim 1, wherein the electronic device comprises a touchscreen device.

5. The method of claim 1, wherein the electronic device comprises a mobile device.

6. The method of claim 1, wherein the electronic device comprises a tablet.

7. The method of claim 1, wherein the electronic device comprises a phone.

8. The method of claim 1, wherein the first clinical domain comprises diagnoses.

9. The method of claim 1, wherein the first clinical domain comprises encounters.

10. The method of claim 1, wherein the first clinical domain comprises procedures.

11. The method of claim 1, wherein the first clinical domain comprises problems.

12. The method of claim 1, wherein the first clinical domain comprises allergies.

13. The method of claim 1, wherein the first clinical domain comprises immunizations.

14. A non-transitory computer-readable storage media containing computer executable instructions that, when executed by a processor of an electronic device, cause the processor to perform acts comprising:
- receiving, at an electronic healthcare records (EHR) application executed by the processor of the electronic device, first user input from a user, the first user input corresponding to login credentials for a user account of the user;
- determining, by the EHR application, a role associated with the user account of the user;
- accessing, by the EHR application, configuration information for a specialty view in a plurality of specialty views, the configuration information for the specialty view including:
  - an indication of with a role assigned to the specialty view;
  - an indication that, for the specialty view, a first clinical domain has a first priority and a second clinical domain has a second priority, wherein the first priority is higher than the second priority; and
  - for the first clinical domain and for the specialty view, an indication that a first vocabulary has a third priority and a fourth vocabulary has a fourth priority, wherein the third priority is higher than the fourth priority;
- comparing, by the EHR application, the role associated with the user account with the role assigned to the specialty view in the configuration information;
- determining, by the EHR application and based on the comparing, that the specialty view in the plurality of specialty views is to be utilized;
- determining, by the EHR application and based on the first priority of the first clinical domain and the second priority of the second clinical domain, an ordering of the first clinical domain and the second clinical domain for display;
- displaying, in an interface of the EHR application presented on an electronic display associated with the electronic device and according to the ordering of the first clinical domain and the second clinical domain, a first identifier for the first clinical domain and a second identifier for the second clinical domain;
- receiving, at the EHR application, second input from the user, the second input corresponding to an indication to access information for the first clinical domain;
- determining, by the EHR application and based on the third priority being higher than the fourth priority, an ordering of clinical items for display; and
- displaying, in the interface of the EHR application and based upon the ordering of the clinical items, an identifier for each of the clinical items.

15. The non-transitory computer-readable storage media of claim 14, wherein the first clinical domain comprises diagnoses.

16. The non-transitory computer-readable storage media of claim 14, wherein the first clinical domain comprises encounters.

17. The non-transitory computer-readable storage media of claim 14, wherein the first clinical domain comprises procedures.

18. The non-transitory computer-readable storage media of claim 14, wherein the first clinical domain comprises problems.

19. The non-transitory computer-readable storage media of claim 14, wherein the first clinical domain comprises allergies.

20. The non-transitory computer-readable storage media of claim 14, wherein the first clinical domain comprises immunizations.

* * * * *